(12) United States Patent
Heidemann et al.

(10) Patent No.: US 6,700,000 B1
(45) Date of Patent: Mar. 2, 2004

(54) METHOD FOR PRODUCING PHTHALIC ANHYDRIDE

(75) Inventors: Thomas Heidemann, Weinheim (DE); Herbert Wanjek, Maxdorf (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/700,452

(22) PCT Filed: May 10, 1999

(86) PCT No.: PCT/EP99/03191
§ 371 (c)(1),
(2), (4) Date: Nov. 15, 2000

(87) PCT Pub. No.: WO99/61433
PCT Pub. Date: Dec. 2, 1999

(30) Foreign Application Priority Data

May 26, 1998 (DE) .......................... 198 23 262

(51) Int. Cl.$^7$ ............................ C07D 307/89
(52) U.S. Cl. ........................ 549/248; 502/353
(58) Field of Search ............... 549/248; 502/353

(56) References Cited

U.S. PATENT DOCUMENTS

| | | | |
|---|---|---|---|
| 3,394,468 A | 7/1968 | Zeller | 34/57 |
| 3,565,829 A | 2/1971 | Friedrichsen | 252/464 |
| 3,684,741 A | 8/1972 | Friedrichsen | 252/435 |
| 3,799,886 A | 3/1974 | Felice | 252/461 |
| 4,046,780 A | 9/1977 | Nakanishi | 260/346.4 |
| 4,077,984 A * | 3/1978 | Blechschmitt et al. | 549/248 |
| 4,203,906 A | 5/1980 | Takada | 260/346.4 |
| 4,284,571 A | 8/1981 | Sato | 260/346.4 |
| 4,342,699 A | 8/1982 | Palmer | 549/259 |
| 4,665,200 A | 5/1987 | Nakanishi | 549/239 |
| 5,229,527 A * | 7/1993 | Ueda et al. | 549/248 |
| 5,608,083 A * | 3/1997 | Fuderer et al. | 549/249 |
| 5,677,261 A | 10/1997 | Tenten | 502/439 |
| 5,792,719 A | 8/1998 | Eberle | 502/178 |

FOREIGN PATENT DOCUMENTS

| | | |
|---|---|---|
| EP | 99 431 | 2/1984 |
| EP | 163 231 | 12/1985 |
| EP | 286 448 | 10/1988 |
| EP | 522 871 | 1/1993 |
| EP | 539 878 | 5/1993 |
| EP | 676 400 | 10/1995 |
| WO | 98/37965 | 9/1998 |
| WO | 98/37967 | 9/1998 |

* cited by examiner

*Primary Examiner*—Joseph K. McKane
*Assistant Examiner*—Golam M M Shameem
(74) *Attorney, Agent, or Firm*—Keil & Weinkauf

(57) ABSTRACT

Phthalic anhydride is prepared by catalytic gas-phase oxidation of xylene and/or naphthalene by a gas comprising molecular oxygen in a fixed bed at elevated temperature and using at least three coated catalysts arranged in superposed zones, which catalysts have a layer of catalytically active metal oxides applied to a core of support material. In the process described, the catalyst activity rises from zone to zone from the gas inlet end to the gas outlet end and the activity of the catalysts of the individual zones is set such that the least active catalyst comprises a lower amount of active composition and, if desired, additionally more alkali metal selected from the group consisting of potassium, rubidium and cesium as dopant than the catalyst of the next zone and the subsequent even more active catalyst comprises the same amount of active composition and even less alkali metal as dopant or a greater amount of active composition and, if desired, less alkali metal as dopant than the catalyst of the second zone, with further conditions.

7 Claims, No Drawings

METHOD FOR PRODUCING PHTHALIC ANHYDRIDE

The present invention relates to a process for preparing phthalic anhydride in which the catalytic gas-phase oxidation of o-xylene and/or naphthalene is carried out over at least three zones of catalysts of increasing activity and in which the increase in activity of the zones is effected in a particular way.

It is known that many carboxylic acids and/or carboxylic anhydrides are prepared industrially by the catalytic gas-phase oxidation of aromatic hydrocarbons such as benzene, the xylenes, naphthalene, toluene and durene in fixed-bed reactors, preferably multitube reactors. This is used to obtain, for example, benzoic acid, maleic anhydride, phthalic anhydride, isophthalic acid, terephthalic acid or pyromellitic anhydride. This is generally carried out by passing a mixture of a gas comprising molecular oxygen, for example air, and the starting material to be oxidized through a plurality of tubes arranged in a reactor. Each of the tubes contains a bed of at least one catalyst. To regulate the temperature, the tubes are surrounded by a heat transfer medium, for example a salt melt. Despite this thermostatting, hot spots in which the temperature is higher than in the remainder of the catalyst bed may occur. These hot spots cause secondary reactions such as total combustion of the starting material or lead to formation of undesirable by-products which can be separated from the reaction product only with difficulty, if at all, for example the formation of phthalide or benzoic acid in the preparation of phtahlic anhydride (PA) from o-xylene. Furthermore, the formation of a pronounced hot spot prevents rapid running-up of the reactor, since the catalyst can be irreversibly damaged above a certain hot spot temperature, so that the loading can only be increased in small steps and the increase has to be monitored very carefully (hereinafter referred to as running-up phase).

To decrease the intensity of these hot spots, it has become customary in industry to arrange catalysts having different activities in zones in the catalyst bed, with the less active catalyst generally being located in the fixed bed in a position where the reaction gas mixture comes into contact with it first, i.e. it is at the gas inlet end of the bed, while the more active catalyst is located toward the end where the gas leaves the catalyst bed (DE A 2546268, EP 286 448, DE 2948163, EP 163 231). The catalysts of differing activity in the catalyst bed can be exposed to the reaction gas at the same temperature, but the two zones comprising catalysts of differing activity can also be thermostatted to different reaction temperatures for contact with the reaction gas (DE A 2830765). According to EP 163 231, a plurality of the measures mentioned can be employed simultaneously for setting the activity structure described. It is known from WO 98/00778 that the addition of temporary activity dampers can lead to a shortening of the running-up phase. In EP 676 400, multistructuring in the reaction of tetraalkylbenzenes to give pyromellitic anhydride has been found to have a positive effect in respect of yield and product purity if the activity structuring is carried out such that the catalyst activity first increases and then decreases again in the flow direction of the gas. Finally, EP 99 431 states that, in the reaction of butane to give maleic anhydride, activity structuring of the catalyst bed has a positive effect on the productivity if the catalyst activity increases stepwise (or ideally continuously) in the flow direction of the gas; the activity structuring can be achieved by many different methods, preferably by dilution with inert material. As a result of the stepwise activity increase, a more homogeneous distribution of the energy liberated by the exothermic reaction can be achieved, so that larger amounts of MA can be produced. Since the reaction is carried out at partial conversion, the activity structuring can be achieved in virtually any way. These teachings cannot be applied to the preparation of PA by oxidation of o-xylene and/or naphthalene since, as is known, phthalic anhydride of good quality is obtained only when the reaction is carried out at full conversion (i.e. >99.9% conversion, based on the starting material used) in order to minimize contamination by undesirable, color-producing components such as phthalide or naphthoquinone and to avoid contamination of the waste gas by residual xylene or residual naphthalene.

EP-A 539 878 discloses a method for production of phthalic anhydride from o-xylene and naphthalene over a two-stage catalyst. The catalysts in both stages are so constructed that an inactive carrier is loaded with vanadium pentoxide, anatase titanium dioxide and also niobium, phosphorus, antimony and at least one element oxide of potassium, rubidium, cesium and thallium, the second-stage catalyst differing from the first-stage catalyst in containing less of said at least one element oxide of potassium, rubidium, cesium and thallium.

Despite the abovementioned proposals for improvement, long running-up times of 2–8 weeks or more have hitherto been necessary. "Running-up time" describes the time which is needed to bring the catalyst to the desired final loading, according to the present state of the art 80 g of o-xylene/ standard $m^3$ of air or more, i.e. to bring the oxidation to the steady state, without the catalyst being damaged irreversibly. Here, particular care has to be taken to ensure that the hot spot does not exceed a certain critical value (usually 450–480° C.), since otherwise the PA selectivity, the PA product quality and the life of the catalyst are very adversely affected.

It is an object of the present invention to find a process for preparing phthalic anhydride in which it is possible to simultaneously achieve all desired parameters such as short running-up time, high yield and low formation of by-products and also good product quality, e.g. a low phthalide content, by a combination of particular catalyst zones.

We have found that this object is achieved by a process for preparing phthalic anhydride by catalytic gas-phase oxidation of xylene and/or naphthalene by a gas comprising molecular oxygen in a fixed bed at elevated temperature and using at least three coated catalysts arranged in superposed zones, which catalysts have a layer of catalytically active metal oxides applied in the form of a shell to a core of support material, in which process the catalyst activity rises from zone to zone from the gas inlet end to the gas outlet end and the activity of the catalysts of the individual zones is set such that the least active catalyst comprises a lower amount of active composition and, if desired, additionally more alkali metal selected from the group consisting of potassium, rubidium and cesium as dopant than the catalyst of the next zone and the subsequent even more active catalyst comprises the same amount of active composition and even less alkali metal as dopant or a greater amount of active composition and, if desired, less alkali metal as dopant than the catalyst of the second zone, with the proviso that a) the least active catalyst on nonporous support material comprises from 5 to 9% by weight, based on the total catalyst, of active composition comprising from 3 to 8% by weight of $V_2O_5$, from 0 to 3.5% by weight of $Sb_2O_3$, from 0 to 0.3% by weight of P, from 0.1 to 0.5% by weight of alkali metal (calculated as metal) and as balance $TiO_2$ in anatase form having a BET surface area (J. Amer. Chem. Soc. 60 (1938), 309 et seq.) of from 18 to 22 $m^2/g$, b) the next more active catalyst has the same composition as catalyst (a) except for an active composition content which is from 1 to 5% by weight (absolute) higher and an alkali metal content which is from 0 to 0.25% by weight (absolute) lower and c) the most active catalyst has the same composition as (a) except for an active composition content which is from 1 to 5% by weight (absolute) higher than in (a) and an alkali metal content which is from 0.15 to 0.4% by weight (absolute) lower than in (a).

Accordingly, the catalyst (a) newest to the gas inlet end always has a lower content of active composition (and possibly also an addition of alkali metal, in particular cesium, which decreases the activity) than the next catalyst (b) which in turn can have the same or a lower content of active composition than the subsequent catalyst (c). If the catalysts (b) and (c) have the same content of active composition, the alkali metal content of catalyst (b) has to be greater than that of catalyst (c). Subject to these conditions, the catalyst (a) has, according to a preferred embodiment, an active composition content of from 6 to 8% by weight comprising from 4 to 8% by weight of $V_2O_5$ and from 0.3 to 0.5% by weight of cs (calculated as Cs), in each case based on the active composition, the catalyst (b) has an active composition content of from 8 to 12% by weight comprising from 0.2 to 0.5% by weight of Cs, based on the active composition, and the catalyst (c) has an active composition content of from 8 to 12% by weight comprising from 0 to 0.3% by weight of Cs, based on the active composition. According to a particularly preferred embodiment, the catalyst (a) has an active composition content of from 7 to 8% by weight comprising from 6 to 8% by weight of $V_2O_5$ and from 0.3 to 0.4% by weight of Cs, in each case based on the active composition, the catalyst (b) has an active composition content of from 9 to 11% by weight comprising from 0.2 to 0.4% by weight of Cs, based on the active composition, and the catalyst (c) has an active composition content of from 9 to 11% by weight comprising from 0.05 to 0.2% by weight of Cs (in each case calculated as Cs), based on the active composition.

In place of mutually delineated zones of the different catalysts, it is also possible to achieve a pseudocontinuous transition between the zones and a pseudocontinuous increase in the activity by having a region in which one catalyst is mixed with the next at the transition from one zone to the next zone.

The catalysts (a), (b) and (c) used for the various zones are known per se and their preparation and composition has been described many times. In brief, these catalysts are generally coated catalysts in which the catalytically active composition is usually applied in the form of a shell to a nonporous support material which is generally inert under the reaction conditions, e.g. quartz ($SiO_2$), porcelain, magnesium oxide, tin dioxide, silicon carbide, rutile, alumina ($Al_2O_3$), aluminum silicate, magnesium silicate (steatite), zirconium silicate or cerium silicate or mixtures of these support materials. The catalytically active constituent of the catalytically active composition of these coated catalysts is generally titanium dioxide in the form of its anatase modification together with vanadium pentoxide. In addition, the catalytically active composition may further comprise small amounts of many other oxidic compounds which act as promoters to influence the activity and selectivity of the catalyst, for example by lowering or increasing its activity. Examples of such promoters are the alkali metal oxides, in particular lithium, potassium rubidium and cesium oxide, thallium(I) oxide, aluminum oxide, zirconium oxide, iron oxide, nickel oxide, cobalt oxide, manganese oxide, tin oxide, silver oxide, copper oxide, chromium oxide, molybdenum oxide, tungsten oxide, iridium oxide, tantalum oxide, niobium oxide, arsenic oxide, antimony oxide, cerium oxide and phosphorus pentoxide. Promoters which reduce the activity and increase the selectivity are, for example, the alkali metal oxides, while oxidic phosphorus compounds, in particular phosphorus pentoxide, increase the activity of the catalyst but reduce its selectivity.

Such coated catalysts are produced according to the processes of DE A 1642938 and DE A 1769998 by spraying an aqueous and/or organic solvent-containing solution or suspension of the constituents of the active composition and/or their precursor compounds, hereinafter referred to as the "slurry", onto the support material in a heated coating drum at elevated temperature until the desired proportion by weight of active composition in the total catalyst has been achieved. According to DE 2106796, coating can also be carried out in fluidized-bed coaters as are mentioned, for example, in DE 1280756. However, spraying in the coating drum or coating in a fluidized bed results in high losses since considerable amounts of the slurry are converted into a mist or part of the active composition already applied is rubbed off again by abrasion and are carried out by the waste gas. Since the proportion of active composition in the total catalyst should generally deviate only slightly from the specified value because the amount of active composition applied and thus the thickness of the shell strongly influence the activity and selectivity of the catalyst, in the production methods indicated the catalyst has to be cooled frequently, taken from the coating drum or the fluidized bed and weighed to determine the amount of active composition applied. If too much active composition is applied to the catalyst support, it is generally not possible for the excess active composition to be carefully removed afterwards without adversely affecting the strength of the shell, in particular without crack formation in the catalyst shell.

To reduce these problems, it has become customary in industry to add organic binders, preferably copolymers, advantageously in the form of an aqueous dispersion, of vinyl acetate/vinyl laurate, vinyl acetate/acrylate, styrene/acrylate, vinyl acetate/maleate or vinyl acetate/ethylene, to the slurry. The amount of binder used is 10–20% by weight, based on the solids content of the slurry (EP 744214). If the slurry is applied to the support without the addition of organic binders, coating temperatures above 150° C. are advantageous. When the above-described binders are added, the usable coating temperatures are, depending on the binder used, from 50 to 450° C. (DE 2106796). The binders applied burn off within a short time after introduction of the catalyst into the reactor and start-up of the reactor. Furthermore, the addition of binder has the advantage that the active composition adheres well to the support, so that transport and charging of these catalysts are made easier.

Further suitable methods of producing coated catalysts for the catalytic gas-phase oxidation of aromatic hydrocarbons to give carboxylic acids and/or carboxylic anhydrides are described in WO 98-00778 and EP A 714700. The layer comprising the catalytically active metal oxides is applied to a support material by first preparing a powder from a solution and/or a suspension of the catalytically active metal oxides and/or their precursor compounds, if desired in the presence of auxiliaries for catalyst production, subsequently applying the powder in the form of a shell to the catalyst support, if desired after conditioning and, if desired, after heat treatment for generating the catalytically active metal oxides, and subjecting the support which has been coated in this way to a heat treatment for generating the catalytically active metal oxides or a treatment to remove volatile constituents.

The conditions of the process for preparing phthalic anhydride from o-xylene and/or naphthalene are likewise known from the literature. In particular, reference may be made to a review in K. Towae, W. Enke, R. Jäckh, N. Bhargana "Phthalic Acid and Derivatives" in Ullmann's Encyclopedia of Industrial Chemistry Vol. A. 20, 1992, 181, which is hereby incorporated by reference. Unlike the process known from the literature reference, the present process enables the "running-up times", i.e. the times required to reach the steady state, to be reduced to, as a rule, from 5 to 20 days. Otherwise, the boundary conditions known from this literature reference and also, for example, from WO-A 98/37967 apply to the steady operating state of the oxidation.

For this purpose, the catalysts are first introduced into the reaction tubes of the reactor which are thermostatted from the outside to the reaction temperature, for example by means of salt melts. The reaction gas is passed over the catalyst bed prepared in this way at generally from 300 to 450° C., preferably from 320 to 420° C. and particularly preferably from 340 to 400° C., at a gauge pressure of generally from 0.1 to 2.5 bar, preferably from 0.3 to 1.5 bar and at a space velocity of generally from 750 to 5000 $h^{-1}$.

The reaction gas passed over the catalyst is generally produced by mixing a gas comprising molecular oxygen, which gas may further comprise suitable reaction moderators and/or diluents such as steam, carbon dioxide and/or nitrogen, with the aromatic hydrocarbon to be oxidized. The gas comprising the molecular oxygen generally comprises from 1 to 100 mol %, preferably from 2 to 50 mol % and particularly preferably from 10 to 30 mol %, of oxygen, from 0 to 30 mol %, preferably from 0 to 10 mol %, of water vapor and from 0 to 50 mol %, preferably from 0 to 1 mol %, of carbon dioxide, balance nitrogen. To produce the reaction gas, the gas comprising the molecular oxygen is generally mixed with from 30 to 150 g of the aromatic hydrocarbon to be oxidized per standard $m^3$ of gas.

EXAMPLES

The anatase used in the examples below typically had the following composition: apart from $TiO_2$, 0.18% by weight of 5, 0.08% by weight of P, 0.24% by weight of Nb, 0.01% by weight of Na, 0.01% by weight of K, 0.004% by weight of Zr, 0.004% by weight of Pb.

Example 1

Production of Catalyst I(a)

700 g of steatite (magnesium silicate) in the form of rings having an external diameter of 8 mm, a length of 6 mm and a wall thickness of 1.5 mm were heated to 210° C. in a coating drum and sprayed with a suspension comprising 400.0 g of anatase having a BET surface area of 21 $m^2/g$, 57.6 g of vanadyl oxalate, 14.4 g of antimony trioxide, 3.3 g of ammonium hydrogen phosphate, 2.60 g of cesium sulfate, 618 g of water and 128 g of formamide until the weight of the layer applied was 7.1% of the total weight of the finished catalyst. The catalytically active composition applied in this way, i.e. the catalyst shell, comprised 0.2% by weight of phosphorus (calculated as P), 7.5% by weight of vanadium (calculated as $V_2O_5$), 3.2% by weight of antimony (calculated as $Sb_2O_3$), 0.4% by weight of cesium (calculated as Cs) and 88.75% by weight of titanium dioxide.

Example 2

Production of Catalyst II (a)

700 g of steatite (magnesium silicate) in the form of rings having an external diameter of 8 mm, a length of 6 mm and a wall thickness of 1.5 mm were heated to 210° C. in a coating drum and sprayed with a suspension comprising 400.0 g of anatase having a BET surface area of 21 $m^2/g$, 57.6 g of vanadyl oxalate, 14.4 g of antimony trioxide, 3.3 g of ammonium hydrogen phosphate, 2.28 g of cesium sulfate, 618 g of water and 128 g of formamide until the weight of the layer applied was 7.5% of the total weight of the finished catalyst. The catalytically active composition applied in this way, i.e. the catalyst shell, comprised 0.2% by weight of phosphorus (calculated as P), 7.5% by weight of vanadium (calculated as $V_2O_5$), 3.2% by weight of antimony (calculated as $Sb_2O_3$), 0.35% by weight of cesium (calculated as Cs) and 88.8% by weight of titanium dioxide.

Example 3

Production of Catalyst III 700 g of steatite (magnesium silicate) in the form of rings having an external diameter of 8 mm, a length of 6 mm and a wall thickness of 1.5 mm were heated to 210° C. in a coating drum and sprayed with a suspension comprising 400.0 g of anatase having a BET surface area of 21 $m^2/g$, 57.6 g of vanadyl oxalate, 14.4 g of antimony trioxide, 3.3 g of ammonium hydrogen phosphate, 2.28 g of cesium sulfate, 618 g of water and 128 g of formamide until the weight of the layer applied was 6.8% of the total weight of the finished catalyst. The catalytically active composition applied in this way, i.e. the catalyst shell, comprised 0.2% by weight of phosphorus (calculated as P), 7.5% by weight of vanadium (calculated as $V_2O_5$), 3.2% by weight of antimony (calculated as $Sb_2O_3$), 0.35% by weight of cesium (calculated as Cs) and 88.8% by weight of titanium dioxide.

Example 4

Production of Catalyst IV (b)

700 g of steatite (magnesium silicate) in the form of rings having an external diameter of 8 mm, a length of 6 mm and a wall thickness of 1.5 mm were heated to 210° C. in a coating drum and sprayed with a suspension comprising 400.0 g of anatase having a BET surface area of 21 $m^2/g$, 57.6 g of vanadyl oxalate, 14.4 g of antimony trioxide, 3.3 g of ammonium hydrogen phosphate, 2.28 g of cesium sulfate, 618 g of water and 128 g of formamide until the weight of the layer applied was 10.5% of the total weight of the finished catalyst. The catalytically active composition applied in this way, i.e. the catalyst shell, comprised 0.2% by weight of phosphorus (calculated as P), 7.5% by weight of vanadium (calculated as $V_2O_5$), 3.2% by weight of antimony (calculated as $Sb_2O_3$), 0.40% by weight of cesium (calculated as Cs) and 88.75% by weight of titanium dioxide.

Example 5

Production of Catalyst V (b)

700 g of steatite (magnesium silicate) in the form of rings having an external diameter of 8 mm, a length of 6 mm and a wall thickness of 1.5 mm were heated to 210° C. in a coating drum and sprayed with a suspension comprising 400.0 g of anatase having a BET surface area of 21 m²/g, 57.6 g of vanadyl oxalate, 14.4 g of antimony trioxide, 3.3 g of ammonium hydrogen phosphate, 2.28 g of cesium sulfate, 618 g of water and 128 g of formamide until the weight of the layer applied was 10.1% of the total weight of the finished catalyst. The catalytically active composition applied in this way, i.e. the catalyst shell, comprised 0.2% by weight of phosphorus (calculated as P), 7.5% by weight of vanadium (calculated as $V_2O_5$), 3.2% by weight of antimony (calculated as $Sb_2O_3$), 0.35% by weight of cesium (calculated as Cs) and 88.8% by weight of titanium dioxide.

Example 6

Production of Catalyst VI 700 g of steatite (magnesium silicate) in the form of rings having an external diameter of 8 mm, a length of 6 mm and a wall thickness of 1.5 mm were heated to 210° C. in a coating drum and sprayed with a suspension comprising 400.0 g of anatase having a BET surface area of 21 m²/g, 57.6 g of vanadyl oxalate, 14.4 g of antimony trioxide, 3.3 g of ammonium hydrogen phosphate, 2.28 g of cesium sulfate, 618 g of water and 128 g of formamide until the weight of the layer applied was 10.6% of the total weight of the finished catalyst. The catalytically active composition applied in this way, i.e. the catalyst shell, comprised 0.2% by weight of phosphorus (calculated as P), 7.5% by weight of vanadium (calculated as $V_2O_5$), 3.2% by weight of antimony (calculated as $Sb_2O_3$), 0.30% by weight of cesium (calculated as Cs) and 88.85% by weight of titanium dioxide.

Example 7

Production of Catalyst VII (c)

700 g of steatite (magnesium silicate) in the form of rings having an external diameter of 8 mm, a length of 6 mm and a wall thickness of 1.5 mm were heated to 210° C. in a coating drum and sprayed with a suspension comprising 400.0 g of anatase having a BET surface area of 21 m²/g, 57.6 g of vanadyl oxalate, 14.4 g of antimony trioxide, 3.3 g of ammonium hydrogen phosphate, 2.28 g of cesium sulfate, 618 g of water and 128 g of formamide until the weight of the layer applied was 10.5% of the total weight of the finished catalyst. The catalytically active composition applied in this way, i.e. the catalyst shell, comprised 0.2% by weight of phosphorus (calculated as P), 7.5% by weight of vanadium (calculated as $V_2O_5$), 3.2% by weight of antimony (calculated as $Sb_2O_3$), 0.10% by weight of cesium (calculated as Cs) and 89.05% by weight of titanium dioxide.

Example 8

Preparation of PA at a Loading of up to 85 g of o-xylene/Standard m³ of Air (According to the Present Invention)

1.00 m of catalyst I(a), 0.60 m of catalyst IV (b) and 1.30 m of catalyst VII (c) were introduced into an iron tube having a length of 3.85 m and an internal diameter of 25 mm. To regulate the temperature, the iron tube was surrounded by a salt melt and a 4 mm thermocouple sheath in which a movable thermocouple was installed served to measure the catalyst temperature. 4.0 standard m³/h of air having loadings of from 0 to 85 g/standard m³ of 98.5% purity by weight o-xylene were passed through the tube from the top downward. At 50–85 g of o-xylene/standard m³ of air, this gave the results summarized in Table 1 ("yield" means the PA obtained in % by weight based on 100%-pure o-xylene; "running-up time" means the number of days required for increasing the loading from 0 to 80 g/standard m³).

Example 9

Preparation of PA at Loadings up to 85 g of o-xylene/Standard m³ of Air (According to the Present Invention)

The procedure of Example 8 is repeated except that the catalysts used are II(a), V(b) and VII(c).

Example 10

Preparation of PA at Loadings up to 85 g of o-xylene/Standard m³ of Air (Comparison)

1.60 m of catalyst IV(b) and 1.30 m of catalyst VII(c) were introduced into an iron tube having a length of 3.85 m and an internal diameter of 25 mm. To regulate the temperature, the iron tube was surrounded by a salt melt and a 4 mm thermocouple sheath in which a movable thermocouple was installed served to measure the catalyst temperature. 4.0 standard m³/h of air having loadings of 98.5% purity by weight o-xylene rising from 0 to about 85 g/standard m³ of air were passed through the tube from the top downward. At 50–85 g of o-xylene/standard m³ of air, this gave the results summarized in Table 1 ("yield"0 means the PA obtained in % by weight based on 100%-pure o-xylene; "running-up time" means the number of days required for increasing the loading from 0 to 80 g/standard m³).

Example 11

Preparation of PA at Loadings up to 85 g of o-xylene/Standard m³ of Air (Comparison)

2.10 m of catalyst I(a) and 0.80 m of catalyst VII(c) were introduced into an iron tube having a length of 3.85 m and an internal diameter of 25 mm. To regulate the temperature, the iron tube was surrounded by a salt melt and a 4 mm thermocouple sheath in which a movable thermocouple was installed served to measure the catalyst temperature. 4.0 standard m³/h of air having loadings of 98.5% purity by weight o-xylene rising from 0 to about 85 g/standard m³ of air were passed through the tube from the top downward. At 50–85 g of o-xylene/standard m³ of air, this gave the results summarized in Table 1 ("yield" means the PA obtained in % by weight based on 100%-pure o-xylene; "running-up time" means the number of days required for. increasing the loading from 0 to 80 g/standard m³).

Example 12

Preparation of PA at Loadings up to 85 g of o-xylene/Standard m³ of Air (Comparison)

2.10 m of a catalyst consisting of a mixture of 75% by weight of catalyst IV(b) and 25% by weight of steatite (magnesium silicate) in the form of rings (having an external diameter of 8 mm, a length of 6 mm and a wall thickness of 1.5 mm) and 0.80 m of catalyst VII(c) were introduced into an iron tube having a length of 3.85 m and an internal diameter of 25 mm. To regulate the temperature, the iron tube was surrounded by a salt melt and a 4 mm thermocouple sheath in which a movable thermocouple was installed served to measure the catalyst temperature. 4.0 standard m³/h of air having loadings of from 0 to 85 g/standard m³ of air of 98.5% purity by weight o-xylene were passed through the tube from the top downward. At 50–85 g of o-xylene/standard m³ of air, this gave the results summarized in Table 1 ("yield" means the PA obtained in % by weight based on 100%-pure o-xylene; "running-up time" means the number of days required for increasing the loading from 0 to 80 g/standard m³).

Example 13

Preparation of PA at Loadings up to 85 g of o-xylene/Standard m³ of Air (Comparison)

The procedure of Example 8 is repeated, except that the catalysts used are III, VI and VII (c).

TABLE 1

| Example: Catalyst combination | Salt bath temperature (° C.) | Running-up time | Average PA yield over 30 days (% by weight) | Average phthalide content in the crude PA over 30 days (mol%) |
|---|---|---|---|---|
| 8: I(a), IV (b), VII (c) | 380–370 | 7 | 111.5 | 0.10–0.19 |
| 9:II(a), V(b), VII (c) | 370–366 | 10 | 113 | 0.15–0.25 |
| 10:Comparison IV(b)/VII(c) | 365–355 | 32 | 112.5 | 0.05–0.22 |
| 11: Comparison I(a)/VII(c) | 380–370 | 10 | 113 | 0.37–0.58 |
| 12:Comparison IV(b) + steatite/VII (c) | 375–365 | 11 | 113 | 0.33–0.55 |
| 13:Comparison III/VI/VIIc | 380–370 | Loading cannot be increased to values above 40 g of o-xylene/ standard m³ of air even over a prolonged period | (see comment under "running-up" time) | (see comment under "running-up" time) |

Example 14

Preparation of PA at Loadings up to 105 g of o-xylene/Standard m3 of Air (According to the Present Invention)

The procedure of Example 8 is repeated, except that 4.0 standard m³/h of air having loadings of 98.5% purity by weight o-xylene of from 85 to about 105 g/standard m³ of air were passed through the tube from the top downward. At 95–105 g of o-xylene/standard m³ of air, this gave the results summarized in Table 2 ("yield" means the PA obtained in % by weight based on 100%-pure o-xylene; "running-up time" means the number of days required for increasing the loading from 80 to 105 g/standard m³).

Example 15

Preparation of PA at Loadings up to 105 g of o-xylene/Standard m³ of Air (According to the Invention)

The procedure of Example 9 is repeated, except that 4.0 standard m³/h of air having loadings of 98.5% purity by weight o-xylene of from 85 to about 105 g/standard m³ of air were passed through the tube from the top downward. At 95–105 g of o-xylene/standard m³ of air, this gave the results summarized in Table 2 ("yield" means the PA obtained in % by weight based on 100%-pure o-xylene; "running-up time" means the number of days required for increasing the loading from 80 to 105 g/standard m³).

Example 16

Preparation of PA at Loadings up to 105 g of o-xylene/Standard m3 of Air (Comparison)

The procedure of Example 11 is repeated, except that 4.0 standard m³/h of air having loadings of 98.5% purity by weight o-xylene of from 85 to about 105 g/standard m³ of air were passed through the tube from the top downward. At 95–105 g of o-xylene/standard m³ of air, this gave the results summarized in Table 2 ("yield" means the PA obtained in % by weight based on 100%-pure o-xylene; "running-up time" means the number of days required for increasing the loading from 80 to 105 g/standard m³).

Example 17

Preparation of PSA at Loadings up to 105 g of o-xylene/Standard m³ of Air (Comparison)

The procedure of Example 12 is repeated, except that 4.0 standard m³/h of air having loadings of 98.5% purity by weight o-xylene of from 85 to about 105 g/standard m³ of air were passed through the tube from the top downward. At 95–105 g of o-xylene/standard m³ of air, this gave the results summarized in Table 2 (yield means the PA obtained in % by weight based on 100%-pure o-xylene; running-up time means the number of days required for increasing the loading from 80 to 105 g/standard m³).

TABLE 2

| Example: Catalyst combination | Salt bath temperature (° C.) | Running-up time | Average PA yield over 30 days (% by weight) | Average phthalide content in the crude PA over 30 days (mol%) |
|---|---|---|---|---|
| 14: I(a)/IV(b)/V II(c) | 375 | 13 | 110 | 0.14–0.19 |
| 15: II(a), V(b), VII (c) | 366 | 15 | 111.5 | 0.14–0.24 |
| 16: Comparison IV (b)/VII (c) | 356–353 | Loading cannot be increased to values above 90 g of o-xylene/ standard m³ of air even over a prolonged period | (see comment under "Running- up time") | (see comment under "Running-up time") |
| 17: Comparison I(a)/VII(c) | 370–366 | Although the loading could be increased to the desired 105 g of o-xylene/ standard m³ of air, high phthalide | (see comment under "Running- up time") | (see comment under "Running-up time") |

TABLE 2-continued

| Example: Catalyst combination | Salt bath temperature (° C.) | Running-up time | Average PA yield over 30 days (% by weight) | Average phthalide content in the crude PA over 30 days (mol%) |
|---|---|---|---|---|
| | | values and significant amounts of xylene of 0.1–0.2% in the waste gas were observed at loadings above 90 g/ standard m³ | | |

What is claimed is:

1. A process for preparing phthalic anhydride by catalytic gas-phase oxidation of xylene and/or naphthalene by a gas comprising molecular oxygen in a fixed bed at elevated temperature, which process comprises conducting the oxidation in the presence of at least three coated catalysts arranged in superposed zones, which catalysts have a layer of a catalytically active composition of metal oxides applied to a core of nonporous support material, the active composition comprising from 3 to 8% by weight of $V_2O_5$, from 0 to 3.5% by weight of $Sb_2O_3$, from 0 to 0.3% by weight of P, alkali metal selected from the group consisting of potassium, rubidium and cesium as a dopant, and as balance $TiO_2$ in anatase form having a BET surface area of from 18 to 22 m²/g, wherein the catalyst activity rises from zone to zone from the gas inlet end to the gas outlet end and the activity of the catalysts of the individual zones is set such that a) the least active catalyst comprises from 5 to 9% by weight, based on the total catalyst, of the active composition and the active composition comprises from 0.1 to 0.5% by weight of alkali metal (calculated as metal);

b) the next more active catalyst comprises from 1 to 5% by weight (absolute) more of the active composition than the catalyst (a), and the active composition comprises from b to 0.25% by weight (absolute) less of alkali metal than the active composition of the catalyst (a); and c) the most active catalyst comprises from 1 to 5% by weight (absolute) more of the active composition than the catalyst (a), and the active composition comprises from 0.15 to 0.4% by weight (absolute) less of alkali metal than the active composition of the catalyst (a).

2. The process of claim 1, wherein cesium is used in amounts of from 0.25 to 0.5% by weight as alkali metal in the catalyst (a).

3. The process of claim 1, wherein the catalyst (c) comprises the same amount or a greater amount of active composition and less alkali metal as dopant than the catalyst (b).

4. The process of claim 1, wherein the catalyst (b) comprises a greater amount of active composition and less alkali metal as dopant than the catalyst (a).

5. The process of claim 1, wherein the catalyst (b) comprises the same amount of active composition and more alkali metal as dopant than the catalyst (c).

6. The process of claim 1, wherein the catalysts (a) to (c) comprise cesium as alkali metal.

7. The process of claim 1, wherein (a) has an active composition content of from 7 to 8% by weight comprising from 6 to 8% by weight of $V_2O_5$ and from 0.3 to 0.4% by weight of Cs, (b) has an active composition content of from 9 to 11% by weight comprising from 0.2 to 0.4% by weight of Cs, and (c) has an active composition content of from 9 to 11% by weight comprising from 0.05 to 0.2% by weight of Cs.

* * * * *

UNITED STATES PATENT AND TRADEMARK OFFICE
CERTIFICATE OF CORRECTION

PATENT NO.     : 6,700,000 B1
DATED          : March 2, 2004
INVENTOR(S)    : Heidemann et al.

It is certified that error appears in the above-identified patent and that said Letters Patent is hereby corrected as shown below:

Column 12,
Line 6, "b" should be -- 0 --.

Signed and Sealed this

Twenty-third Day of November, 2004

JON W. DUDAS
*Director of the United States Patent and Trademark Office*